United States Patent [19]

Yellin et al.

[11] 4,309,435

[45] Jan. 5, 1982

[54] ANTISECRETORY GUANIDINE DERIVATIVES AND PHARMACEUTICAL COMPOSITIONS CONTAINING THEM

[75] Inventors: Tobias O. Yellin, Wallingford, Pa.; David J. Gilman, Macclesfield, England

[73] Assignees: Imperial Chemical Industries Ltd., London, England; ICI Americas Inc., Wilmington, Del.

[21] Appl. No.: 83,361

[22] Filed: Oct. 10, 1979

[30] Foreign Application Priority Data

Oct. 16, 1978 [GB] United Kingdom ............... 40704/78

[51] Int. Cl.³ .................. C07D 277/20; C07D 285/08
[52] U.S. Cl. .................... 424/269; 424/270; 424/272; 548/181; 548/186; 548/128; 548/134; 548/143; 548/235; 548/337; 548/131
[58] Field of Search ............... 548/181, 186, 128, 134, 548/143, 235, 337, 131; 424/272, 269, 270

[56] References Cited

U.S. PATENT DOCUMENTS 4,022,797 5/1977 Durant et al. ................. 548/186
4,093,729 6/1978 Durant et al. ................. 548/186

FOREIGN PATENT DOCUMENTS 857218 1/1975 Belgium .
849810 12/1975 Belgium .
864992 3/1977 Belgium .
857219 1/1978 Belgium .
1431589 4/1976 United Kingdom .
1493931 11/1977 United Kingdom .
1496787 1/1978 United Kingdom .
1531221 11/1978 United Kingdom .

Primary Examiner—Nicholas S. Rizzo
Attorney, Agent, or Firm—John M. Sheehan; David J. Levy

[57] ABSTRACT

The invention relates to a guanidine derivative of the formula I:

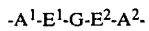

Het¹-(CH₂)ₘ-Y¹-(CH₂)ₙ-NR¹-A-NR²-(CH₂)_q-Y²-(CH₂)_p-Het²    I in which Y¹ and Y² are O, S, direct bonds, CH₂ or SO; m and p are 0 to 4, n and q are 1 to 4, provided that when Y¹ or Y² is O, S or SO, m or p is 1 to 4 and provided that when Y¹ or Y² is O or SO, n or q is 2 to 4; one of R¹ and R² is hydrogen and the other is hydrogen or C$_{(1-6)}$alkyl; A is 3,4-dioxocyclobuten-1,2-diyl or C=Z in which Z is S, O, NCN, NNO₂, CHNO₂, NCONH₂, C(CN)₂, NCOR³, NCO₂R³, NSO₂R³ or NR⁴ in which R³ is C$_{(1-6)}$alkyl or C$_{(6-12)}$aryl and R⁴ is hydrogen or C$_{(1-6)}$alkyl or when R¹ and R² are hydrogen A is

-A¹-E¹-G-E²-A²-    II in which A¹ and A² are 3,4-dioxocyclobuten-1,2-diyl or C=Z¹ and C=Z² in which Z¹ and Z² are the same as Z, E¹ and E² are O or S or NH optionally substituted by C$_{(1-10)}$alkyl, C$_{(3-10)}$alkenyl, C$_{(3-10)}$alkynyl, C$_{(3-8)}$cycloalkyl, C$_{(2-6)}$(primary hydroxy)alkyl, C$_{(3-10)}$alkoxyalkyl, C$_{(3-10)}$alkylamino or C$_{(3-10)}$dialkylamino and G is C$_{(2-12)}$alkylene, C$_{(4-12)}$*alkenylene*, C$_{(4-12)}$alkynylene or C$_{(3-12)}$hydroxyalkylene; Het¹ is oxazol-4-yl, thiazol-4-yl or imidazol-4-yl substituted in the 2-position by:

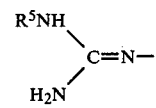

III or Het¹ is 1,2,4-thiadiazol-3-yl or 1,2,4-oxadiazol-3-yl substituted in the 5-position by radical III in which R⁵ is hydrogen, C$_{(1-10)}$alkyl, C$_{(1-6)}$alkanoyl or C$_{(7-11)}$aroyl; Het² is same as Het¹ or an unfused N-containing 5- or 6-membered monocyclic heterocyclic ring optionally substituted by C$_{(1-6)}$alkyl, C$_{(1-6)}$alkoxy, OH, CF₃, HOCH₂, NH₂ or halogen or Het² is

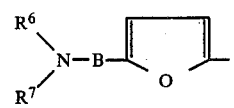

IV in which B is a straight or branched chain C$_{(1-6)}$alkylene and R⁶ and R⁷ are hydrogen, C$_{(1-8)}$alkyl, C$_{(3-10)}$-alkoxyalkyl, C$_{(3-10)}$alkylaminoalkyl, C$_{(3-10)}$dialkylaminoalkyl, or C$_{(7-12)}$phenylalkyl optionally substituted on the phenyl ring by C$_{(1-6)}$alkyl, C$_{(1-6)}$alkoxy, or halogen or R⁶ and R⁷ are joined to form a 5- or 6-membered saturated ring optionally containing O or N, the N substituted by hydrogen or C$_{(1-6)}$alkyl; provided that when R¹ and R² are hydrogen and A is C=NH, Y¹ and/or Y² is S, and that when R¹ and R² are hydrogen, A is C=NH and Het² is imidazole, the number of atoms in the chain:

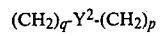

(CH₂)_q-Y²-(CH₂)_p    V is at least 4; and the salts thereof.

11 Claims, No Drawings

ANTISECRETORY GUANIDINE DERIVATIVES AND PHARMACEUTICAL COMPOSITIONS CONTAINING THEM

This invention relates to heterocyclic derivatives which are histamine H-2 antagonists and which inhibit gastric acid secretion.

It is postulated that the physiologically-active compound histamine which occurs naturally within the animal body, is able to combine, in the course of exerting its activity, with certain specific receptors of which there are at least two distinct and separate types. The first has been named the H-1 receptor (Ash and Schild, *Brit. J. Pharmac.,* 1966, 27, 427) and the action of histamine at this receptor is blocked (antagonized) by classical "antihistamine" drugs such as mepyramine. The second histamine receptor has been named the H-2 receptor (Black et al., *Nature,* 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In United Kingdom Patent Nos. 1,421,792, 1,431,589 and 1,493,931 and Belgian Patent Nos. 843,839, 843,840 and 844,503 there are described histamine H-2 receptor antagonists which have carbon and carbon-sulphur chains incorporating in the middle portion one or two modified guanidine residues, both ends of the chains being attached to heterocyclic ring systems. It has now been discovered that if a guanidino radical is directly attached to one or both of the heterocyclic ring systems in these molecules, there are produced potent histamine H-2 antagonists.

According to the invention there is provided a guanidine derivative of the formula I:

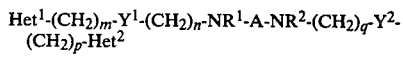

in which $Y^1$ and $Y^2$, which may be the same or different, are oxygen or sulphur atoms, direct bonds or methylene or sulphinyl radicals; m and p, which may be the same or different, are 0 to 4, and n and q, which may be the same or different, are 1 to 4, provided that when $Y^1$ or $Y^2$ is an oxygen or sulphur atom or a sulphinyl radical, m or p respectively is 1 to 4 and provided that when $Y^1$ or $Y^2$ is an oxygen atom or a sulphinyl radical, n or q respectively is 2 to 4; one of $R^1$ and $R^2$ is a hydrogen atom and the other is a hydrogen atom or an alkyl radical of 1 to 6 carbon atoms; A is a 3,4-dioxocyclobuten-1,2-diyl radical or a radical of the formula C=Z in which Z is a sulphur or oxygen atom or a radical of the formula NCN, $NNO_2$, $CHNO_2$, $NCONH_2$, $C(CN)_2$, $NCOR^3$, and $NCO_2R^3$, $NSO_2R^3$ or $NR^4$ in which $R^3$ is an alkyl radical of 1 to 6 carbon atoms, an aryl radical of 6 to 12 carbon atoms or an alkylphenyl radical of 7 to 12 carbon atoms and $R^4$ is a hydrogen atom or an alkyl radical of 1 to 6 carbon atoms, or when $R^1$ and $R^2$ are both hydrogen atoms —A— may represent a radical of the formula II:

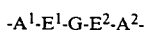

in which $A^1$ and $A^2$, which may be the same or different, are 3,4-dioxocyclobuten-1,2-diyl radicals or radicals of the formula C=$Z^1$ and C=$Z^2$ respectively in which $Z^1$ and $Z^2$, which may be the same or different, have one of the values given above for Z; $E^1$ and $E^2$, which may be the same or different, are oxygen or sulphur atoms or NH radicals, the NH radicals being optionally substituted by alkyl radicals of 1 to 10 carbon atoms, alkenyl or alkynyl radicals of 3 to 10 carbon atoms in which the double or triple bond respectively is separated from the nitrogen atom to which the radical is attached by at least one carbon atom, cycloalkyl radicals of 3 to 8 carbon atoms, (primary hydroxy)alkyl radicals of 2 to 6 carbon atoms, alkoxyalkyl radicals of 3 to 10 carbon atoms in which the oxygen atom is separated from the nitrogen atom to which the radical is attached by at least two carbon atoms, or alkylamino or dialkylamino radicals of 3 to 10 and 4 to 10 carbon atoms respectively in which the nitrogen atom is separated from the nitrogen atom to which the radical is attached by at least two carbon atoms; and G is an alkylene radical of 2 to 12 carbon atoms, an alkenylene or alkynylene radical of 4 to 12 carbon atoms in which the double and triple bonds respectively are separated from $E^1$ and $E^2$ by at least one carbon atom, or a hydroxyalkylene radical of 3 to 12 carbon atoms in which the hydroxy substituent is carried on a carbon atom which is separated from $E^1$ and $E^2$ by at least one carbon atom; $Het^1$ is an oxazol-4-yl, thiazol-4-yl or imidazol-4-yl radical substituted in the 2-position by a radical of the formula III:

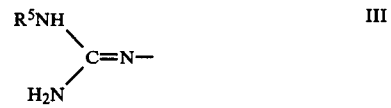

or $Het^1$ is a 1,2,4-thiadiazol-3-yl or 1,2,4-oxadiazol-3-yl radical substituted in the 5-position by a radical of the formula III, in which $R^5$ is a hydrogen atom, an alkyl radical of 1 to 10 carbon atoms, an alkanoyl radical of 1 to 6 carbon atoms or an aroyl radical of 7 to 11 carbon atoms; $Het^2$ is independently one of the values given above for $Het^1$ or is an unfused nitrogen-containing 5- or 6-membered monocyclic heterocyclic ring which is optionally substituted by an alkyl or alkoxy radical of 1 to 6 carbon atoms, a hydroxy, trifluoromethyl, hydroxymethyl or amino radical or by a halogen atom, or $Het^2$ is a radical of the formula IV:

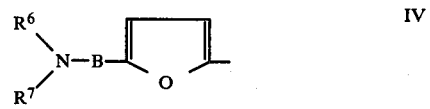

in which B is a straight- or branched-chain alkylene radical of 1 to 6 carbon atoms; and $R^6$ and $R^7$, which may be the same or different, are hydrogen atoms or alkyl radicals of 1 to 8 carbon atoms, alkenyl or cycloalkyl radicals of 3 to 8 carbon atoms, alkoxyalkyl of 3 to 10 carbons, alkylaminoalkyl of 3 to 10 carbons or dialkylaminoalkyl of 4 to 10 carbons radicals in which the oxygen and nitrogen atoms respectively are separated from the nitrogen atom of $NR^6R^7$ by at least two carbon atoms, or phenylalkyl radicals of 7 to 12 carbon atoms optionally substituted on the phenyl ring by an alkyl or alkoxy radical of 1 to 6 carbon atoms or by a halogen atom; or $R^6$ and $R^7$ may be joined together to form a 5- or 6-membered saturated ring which may optionally contain an oxygen or additional nitrogen atom, the additional nitrogen atom being substituted by a hydrogen atom or an alkyl radical of 1 to 6 carbon atoms; provided that when $R^1$ and $R^2$ are both hydrogen atoms and A is C=NH, $Y^1$ and/or $Y^2$ is a sulphur atom, and that when $R^1$ and $R^2$ are both hydrogen atoms, A is C=NH and $Het^2$ is imidazole, the number of atoms in the chain represented by formula V:

$$(CH_2)_q\text{-}Y^2\text{-}(CH_2)_p \qquad \qquad V$$

is at least four; and the pharmaceutically-acceptable acid addition salts thereof.

It is to be understood that, in the above formulae I, II and III and throughout this specification, although the double bonds have been inserted in particular positions, various other tautomeric forms are possible, and this invention includes such tautomeric forms within its scope, in terms of the compound and composition of the invention and in terms of the manufacturing processes.

A particular value for $R^1$ and $R^2$ is a hydrogen atom or a methyl radical.

A particular value for $R^3$ is a methyl, phenyl or p-tolyl radical.

A particular value for $R^4$ is a hydrogen atom or a methyl radical.

A particular value for the optional substituent on $E^1$ and $E^2$ when it is an NH radical is a methyl, ethyl, n-propyl, i-propyl, n-hexyl, allyl, propargyl, cyclopropyl, cyclohexyl, 2-hydroxyethyl, 3-hydroxypropyl, 2-methoxyethyl, 2-methylaminoethyl or 2-dimethylaminoethyl radical.

A particular value for G is an ethylene, trimethylene, tetramethylene, but-2-enylene, but-2-ynylene or 2-hydroxytrimethylene radical.

A particular valve for $R_5$ is a hydrogen atom or a methyl, n-butyl, acetyl or benzoyl radical.

A particular value for $Het^2$ is an oxazol-4-yl, thiazol-4-yl or imidazol-4-yl radical substituted in the 2-position by a radical of the formula III given above in which $R^5$ is a hydrogen atom or a methyl, n-butyl, acetyl or benzoyl radical or $Het^2$ is an imidazole, thiazole, isothiazole, oxazole, isoxazole, pyrazole, triazole, thiadiazole, pyridine, pyrimidine, pyrazine or pyridazine ring optionally substituted by a methyl, methoxy, hydroxy, trifluoromethyl, hydroxymethyl or amino radical or by a fluorine, chlorine, bromine or iodine atom, or $Het^2$ is a radical of the formula IV given above in which B is a methylene radical, $R^6$ and $R^7$ are hydrogen atoms or methyl, allyl, cyclohexyl, 2-methoxyethyl, 2-methylaminoethyl, 2-dimethylaminoethyl, phenethyl optionally substituted on the phenyl ring by a methyl or methoxy radical or by a fluorine, chlorine, bromine or iodine atom or $R^6$ and $R^7$, when alkyl, are joined to form a 5- or 6-membered ring which may contain an oxygen or another nitrogen, e.g. joined to form a morpholine, pyrrolidine, piperidine, piperazine or N-methylpiperazine ring.

The following are 7 preferred features of the guanidine derivative of the formula I. When any one of these features is taken, either singly or in combination, with the other general features of the guanidine derivative of the formula I listed above, there are obtained preferred sub-groups of compounds within the above general definition.

1. A is a 3,4-dioxocyclobuten-1,2-diyl radical or a radical of the formula C=Z in which Z is a radical of the formula NCN, $NNO_2$, $CHNO_2$ or $NCONH_2$.
2. $Het^1$ and $Het^2$ are the same, $Y^1$ and $Y^2$ are the same, $R^1$ and $R^2$ are the same, m and p are the same and/or n and q are the same.
3. $R^5$ is a hydrogen atom.
4. $Het^1$ is a 2-guanidinothiazol-4-yl or 5-guanidino-1,2,4-thiadiazol-3-yl radical.
5. $Y^1$ is a sulphur atom or methyl radical, m is 1 and n is 2.
6. $Y^2$ is a sulphur atom or methylene radical, p is 1 and q is 2.
7. $Het^2$ is a 2-guanidinothiazol-4-yl, 5-guanidino-1,2,4-thiadiazol-3-yl, 5-methylimidazol-4-yl or 5-dimethylaminomethylfuran-2-yl radical.

Specific compounds of the invention are set out in the Examples.

The following is preferred group of compounds:

1,3-bis[2-(2-guanidinothiazol-4-ylmethylthio)ethyl]thiourea;

1,2-bis[4-(2-guanidinothiazol-4-yl)butylamino]cyclobutene-3,4-dione;

1-[2-(2-guanidinothiazol-4-ylmethylthio)ethylamino]-2-[4-(2-guanidinothiazol-4-yl)butylamino]cyclobutene-3,4-dione;

1-[2-(2-guanidinothiazol-4-ylmethylthio)ethyl]-3-[2-(5-methylimidazol-4-ylmethylthio)ethyl]thiourea;

1-[2-(2-guanidinathiazol-4-ylmethylthio)ethyl]-3-[3-(imidazol-4-yl)propyl]thiourea;

2-guanidino-4-[2-(2-cyano-3-[2-(5-dimethylaminomethylfuran-2-ylmethylthio)ethyl]guanidino)ethylthiomethyl]thiazole;

1-[2-(2-guanidinothiazol-4-ylmethylthio)ethyl]-3-[3-(2-cyano-3-(2-(2-guanidinothiazol-4-ylmethylthio)ethyl)-guanidino)-2-hydroxypropyl]thiourea;

and the pharmaceutically-acceptable acid addition salts thereof.

A suitable pharmaceutically-acceptable acid-addition salt of the guanidine derivative of the invention is, for example, a salt formed with hydrochloric, hydrobromic, phosphoric, sulphuric, citric or maleic acid.

The guanidine derivative of the invention may be manufactured by methods known in themselves for the manufacture of chemically analogous compounds. Thus the following processes, $Het^1$, $Het^2$, $Y^1$, $Y^2$, $R^1$, $R^2$, $R^3$, $R^4$, $R^5$, $R^6$, $R^7$, m, n, p and q having the meanings stated above unless indicated otherwise are provided as further features of the invention.

The process of the invention is characterized by: (a) reaction of a compound of the formula VI or VII:

$$Het^1\text{-}(CH_2)_m\text{-}Y^1\text{-}(CH_2)_n\text{-}NR^1\text{-}A\text{-}R^8 \qquad VI$$

$$\text{or } R^8\text{-}A\text{-}NR^2\text{-}(CH_2)_q\text{-}Y^2\text{-}(CH_2)_p\text{-}Het^2 \qquad VII$$

in which $R^8$ is a displaceable radical with a compound of the formula VIII or IX:

$$HNR^2\text{-}(CH_2)_q\text{-}Y^2\text{-}(CH_2)_p\text{-}Het^2 \qquad VIII$$

$$\text{or } Het^1\text{-}(CH_2)_m\text{-}Y^1\text{-}(CH_2)_n\text{-}NR^1H \qquad IX$$

respectively; (b) for those compounds in which $Het^1$ and $Het^2$, $Y^1$ and $Y^2$, m and p and n and q are the same, $R^1$ and $R^2$ are hydrogen atoms and A is a radical of the formula C=Z in which Z is a sulphur or oxygen atom, reaction of a compound of the formula X:

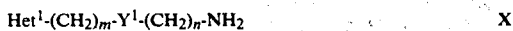

$$\text{Het}^1\text{-}(CH_2)_m\text{-}Y^1\text{-}(CH_2)_n\text{-}NH_2 \qquad X$$

with carbon disulphide, phosgene, carbonyl di-imidazole or thiocarbonyl di-imidazole; (c) for those compounds in which Z is a sulphur or oxygen atom, reaction of a compound of the formula XI or XII:

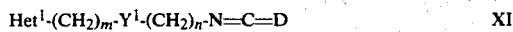

$$\text{Het}^1\text{-}(CH_2)_m\text{-}Y^1\text{-}(CH_2)_n\text{-}N{=}C{=}D \qquad XI$$

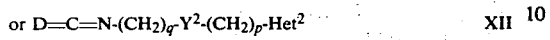

$$\text{or } D{=}C{=}N\text{-}(CH_2)_q\text{-}Y^2\text{-}(CH_2)_p\text{-}\text{Het}^2 \qquad XII$$

in which D is a sulphur or oxygen atom with a compound of the formula VIII or IX respectively; (d) for those compounds in which A is a radical of the formula C=Z in which Z is a radical of the formula NCN, NCOR³, NCO₂R³ or NSO₂R³, reaction of a compound of the formula XIII or XIV:

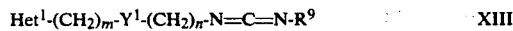

$$\text{Het}^1\text{-}(CH_2)_m\text{-}Y^1\text{-}(CH_2)_n\text{-}N{=}C{=}N\text{-}R^9 \qquad XIII$$

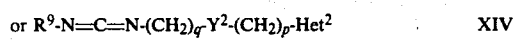

$$\text{or } R^9\text{-}N{=}C{=}N\text{-}(CH_2)_q\text{-}Y^2\text{-}(CH_2)_p\text{-}\text{Het}^2 \qquad XIV$$

in which $R^9$ is a radical of the formula CN, COR³, CO₂R³ or SO₂R³ with a compound of the formula VIII or IX respectively; or (e) for those compounds in which A has the formula II in which $E^1$ and $E^2$ are optionally substituted NH radicals, reaction of a compound of the formula XV or XVI:

$$\text{Het}^1\text{-}(CH_2)_m\text{-}Y^1\text{-}(CH_2)_n\text{-}NH\text{-}A^1\text{-}NR^{10}\text{-}G\text{-}NHR^{11} \qquad XV$$

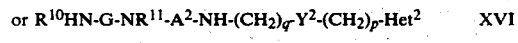

$$\text{or } R^{10}HN\text{-}G\text{-}NR^{11}\text{-}A^2\text{-}NH\text{-}(CH_2)_q\text{-}Y^2\text{-}(CH_2)_p\text{-}\text{Het}^2 \qquad XVI$$

in which $R^{10}$ and $R^{11}$, which may be the same or different, are hydrogen atoms or alkyl, alkenyl, alkynyl, cycloalkyl, (primary hydroxy)alkyl, alkoxyalkyl or alkylaminoalkyl radicals with a compound of the formula VII or VI respectively in which $R^8$ is a displaceable radical, $R^1$ and $R^2$ are hydrogen atoms and A is other than a radical of the formula II.

When the process of the invention yields the compound of the formula I in the form of the free base and an acid-addition salt is required, the compound of the formula I in the free base form is reacted with an acid which affords a pharmaceutically-acceptable anion.

Process (a) may be carried out using one equivalent, or an excess, of the compound of the formula VIII or IX, optionally in the presence of a diluent or solvent such as water, methanol, ethanol, acetonitrile or dimethyl formamide or a mixture of any two of these. The reaction may be carried out at ambient temperature and it may be accelerated or completed by the appliction of heat, for example by heating to the boiling point of the diluent or solvent. $R^8$ may, for example, be an alkoxy or alkylthio radical of 1 of 6 carbon atoms, for example a methoxy, ethoxy or methylthio radical.

Process (b) may be carried out in the presence of a diluent or solvent such as methanol, ethanol or dimethyl formamide. The reaction may be carried out at ambient temperature and it may be accelerated or completed by the application of heat, for example by heating to the boiling point of the diluent or solvent.

Process (c) may be carried out in the presence of a diluent or solvent such as methanol, ethanol or dimethyl formamide. When D is an oxygen atom, a non-hydroxylic diluent or solvent must be used. The reaction is conveniently conducted at ambient temperature.

Process (d) may be carried out in the presence of a diluent or solvent such as dimethyl formamide. The reaction is conveniently carried out at ambient temperature. The carbodi-imide starting materials of the formula XIII or XIV are preferably prepared in situ.

When Het¹ or Het² contains an oxazole ring substituted by a radical of the formula III, the starting material of the formula VI, VII, VIII or IX (for use in process (a)), or X (for use in process (b)), in which A is other than a radical of the formula II, may be prepared, for example, as described in Belgian Patent No. 866,155.

When Het¹ or Het² contains a thiazole or imidazole ring substituted by a radical of the formula III, the starting material of the formula VI, VII, VIII, IX or X in which A is other than a radical of the formula II may be prepared, for example, as described in Belgian Patent No. 866,156 which is the equivalent of U.S. Pat. Nos. 4,165,377 and 4,165,378, both issued Aug. 21, 1979 and both assigned to the assignee of the present invention.

When Het¹ or Het² contains a thiadiazole ring substituted by a radical of the formula III, the starting material of the formula VI, VII, VIII, IX or X in which A is other than a radical of the formula II may be prepared, for example, as described in U.S. Patent Application Ser. No. 36,360 filed May 7, 1979 and assigned to the asignee of the present invention.

When Het¹ or Het² contains an oxadiazole ring substituted by a radical of the formula III, the starting material of the formula VI, VII, VIII, IX or X in which A is other than a radical of the formula II may be prepared, for example, as described in U.S. Patent Application Ser. No. 36,361 filed May 7, 1979 and assigned to the asignee of the present invention.

When Het² is other than one of the values given for Het¹ and is also other than a radical of the formula IV, the starting material of the formula VII or VIII in which A is other than a radical of the formula II may be prepared, for example, as described in United Kingdom Patent Nos. 1,338,169 and 1,397,436.

When Het² is other than one of the values given for Het¹ and is also other than a radical of the formula IV, the starting material of the formula VII in which A is a radical of the formula II may be prepared, for example, as described in United Kingdom Patent No. 1,493,931.

When Het² is a radical of the formula IV, the starting material of the formula VII or VIII in which A is other than a radical of the formula II may be prepared for example as described in Belgian Patent No. 857,388.

When A is a radical of the formula II, the starting material of the formula VI or VII may be prepared, for example, by reaction of a compound of the formula IX or VIII respectively with a compound of the formula XVII:

$$R^8\text{-}A^1\text{-}E^1\text{-}G\text{-}E^2\text{-}A^2\text{-}R^8 \qquad XVII$$

in which $R^8$ is a displaceable radical.

The starting material of the formula XI or XII (for use in process (c)) may be prepared, for example, by reaction of the compound of the formula IX or VIII in which $R^1$ and $R^2$ are hydrogen atoms with thiophosgene or phosgene, for example as illustrated in Example 5.

The starting material of the formula XIII or XIV (for use in process (d)) may be prepared, for example, by reaction of a compound of the formula XVIII or XIX:

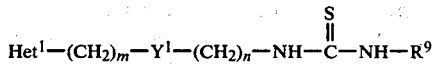

$$\text{Het}^1-(CH_2)_m-Y^1-(CH_2)_n-NH-\overset{S}{\underset{\|}{C}}-NH-R^9 \quad \text{XVIII}$$

or

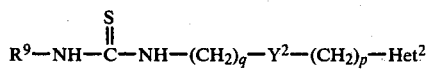

$$R^9-NH-\overset{S}{\underset{\|}{C}}-NH-(CH_2)_q-Y^2-(CH_2)_p-\text{Het}^2 \quad \text{XIX}$$

respectively with silver nitrate, for example as illustrated in Example 8.

The starting material of the formula XV or XVI (for use in process (e)) may be prepared, for example by reaction of a compound of the formula VI or VII in which $R^1$ and $R^2$ are hydrogen atoms and A is other than a radical of the formula II with a compound of the formula (XX):

$$R^{10}HN\text{-}G\text{-}NHR^{11} \quad \text{XX}$$

for example as illustrated in Example 10.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastro-intestinal bleeding due to trauma.

The histamine H-2 antagonist activity may be demonstrated on standard tests, for example by the ability of the compound of the formula I to inhibit the histamine-induced positive chronotropic response in the spontaneously beating right atrium of the guinea pig or by its ability to inhibit the histamine-induced increase in the level of cyclic AMP (in the presence of a phosphodiesterase inhibitor) in a free cell suspension obtained from canine gastric mucosa.

The guinea pig atrium test is carried out as follows:

A guinea pig right atrium is suspended at 1 g tension (isometric) in a thermostatically-controlled (30° C.) tissue bath (25 ml) containing oxygenated (95% $O_2$; 5% $CO_2$) Krebs-Hanseleit buffer (pH 7.4). The tissue is allowed to stabilize over 1 hour during which time it is washed 2–4 times. Individual contractions are recorded with a force-displacement transducer through a strain gauge coupler, and instantaneous rates are monitored with a cardiotachometer. A control response to 1 $\mu$M histamine is obtained after which the tissue is washed 3 times and allowed to re-equilibrate to basal rate. After re-equilibration for 15 minutes, the test compound is added to the desired final concentration. Ten minutes after addition of the compound, histamine (1 $\mu$M) is again added and the response to histamine in the presence of antagonist is compared to the histamine control response. The result is expressed as a percentage of the histamine control response. Thereafter the apparent dissociation constant of the H-2 antagonist is determined by standard procedures. All the compounds exemplified in this specification are active on the guinea pig atrium test at or below a bath concentration of 10 $\mu$M.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats, cats or dogs provided with gastric fistulae and whose gastric secretion is stimulated by the administration of a secretagogue, for example, pentagastrin or histamine.

The test in dogs is carried out as follows:

A female pure bred beagle (9–12 kg) having a chronic gastric fistula is fastened overnight with water ad lib. During the experiment the dog is lightly restrained in a standing position. When studying the test compound by the intravenous route, the fistula is opened and, after ascertaining the absence of basal secretion over a period of 30 minutes, a continuous intravenous infusion of secretagogue (0.5 $\mu$mole/kg/hour of histamine or 2 $\mu$g/kg/hour pentagastrin) in saline (15 ml/hour) is begun. Gastric acid samples are collected every 15 minutes. The volume of each sample is measured and a 1 ml aliquot is titrated to neutrality with 0.1 N NaOH to determine acid concentration. When a plateau of secretion is reached (1–2 hours), the test compound is administered intravenously in saline and gastric acid samples are collected for a further 2–3 hours during which time the infusion of the secretagogue continues uninterrupted.

When studying the test compound by the intragastric route, the absence of basal secretion over a period of 30 minutes is ascertained and the test compound, contained in 25 ml of 0.5% w/v hydroxypropyl methylcellulose and 0.1% w/v 'Tween' 80 in water 80 in water ('Tween' is a Trademark), is instilled into the stomach through a fistula dosing plug. One hour later, the fistula is re-opened and intravenous infusion of a secretagogue, as described above, is immediately begun. Gastric acid samples are measured as described above and the approach of acid secretion to a plateau is compared to that of a control animal which is dosed intratgastrically only with the dosing vehicle.

When studying the test compound by the oral route, it is administered in a gelatin capsule washed down with 15 ml of water. One hour later, the fistula is opened and intravenous infusion of the secretagogue is immediately begun. Gastric acid samples are measured as above and the approach of acid secretion to a plateau is compared to that of an undosed control animal.

The results obtained in the atrium test are predicitive of activity in the dog test.

No overt toxicity or side effects were noted during the dog tests.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspensions, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide-magnesium hydroxide mixtures; antipepsin compounds, for example pepstatin; other histamine H-2 antagonists, for example cimetidine; ulcer healing agents, for example carbenoxolone or bismuth salts; anti-inflammatory agents, for example ibuprofen, indomethacin, naproxen or aspirin; prostaglandins, for example 16,16-dimethylprostaglandin $E_2$; classical antihistamines (histamine H-1 antagonists), for example mepyramine or diphenhydramine; anticholinergic agents, for example atropine or propantheline bromide; and anxiolytic agents, for example diazepam, chlordiazepoxide or phenobarbital.

The pharmaceutical composition of the invention for topical administration may also contain, in addition to the guanidine derivative, one or more classical antihistamines (histamine H-1 antagonists), for example mepyramine or diphenhydramine and/or one or more steroidal anti-inflammatory agents, for example fluocinolone or triamcinolone.

A topical formulation may contain from about 1 to 10% w/w of the guanidine derivative of the invention. A preferred pharmaceutical composition of the invention is one suitable for oral administration in unit dosage form, for example a tablet or capsule which contains from about 1 mg to 500 mg of the guanidine derivative, or one suitable for intravenous, subcutaneous or intramuscular injection for example a sterile injectable containing from about 0.1% to 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency of the guanidine derivative of the present invention relative to cimetidine. Thus each patient will receive an oral dose of from about 2.5 mg to 1500 mg and preferably from about 20 mg to 200 mg of quanidine derivative or an intravenous subcutaneous or intramuscular dose of from about 0.25 mg to 150 mg and preferably from about 2 mg to 20 mg of the guanidine derivative, the composition being administered 2 to 4 times per day. The rectal dose will be approximately the same as the oral dose. The composition may be administered less frequently when it contains an amount of guanidine derivative which is a multiple of the amount which is effective when given 2 to 4 times per day.

The invention is illustrated, but not limited by the following Examples in which the temperatures are in degrees Centigrade:

EXAMPLE 1

A mixture of 2-quanidino-4-[(2-aminoethyl)-thiomethyl]thiazole dihydrochloride (1.03 g), triethylamine (0.73 g), carbon disulphide (0.17 g) and ethanol (10 ml) was heated under reflux for 18 hours; it was then cooled and evaporated to dryness. The residue was suspended in water (50 ml) containing aqueous ammonia (s.g.=0.88, 1 ml) and the mixture extracted with ethyl acetate (2×25 ml). The combined organic extracts were washed with water (50 ml) and then extracted with 1 N aqueous hydrochloric acid. The aqueous extract was washed with ethyl acetate (25 ml), basified by addition of excess aqueous ammonia (s.g. 0.88) and extracted with ethyl acetate (2×25 ml). The combined extracts were washed with water (100 ml), dried (MgSO$_4$), filtered and evaporated to dryness. The residue was dissolved in a mixture of isopropanol (5 ml) and ethyl acetate (20 ml) and the solution stirred with decolorizing charcoal (1 g) for half an hour. The solution was filtered, and to it was added a solution of hydrogen chloride in isopropanol. The resulting white precipitate was filtered off and washed with ethyl acetate to give a sticky white solid. This was dissolved in methanol (5 ml) and the solution was filtered and diluted with ethyl acetate until slightly cloudy. The mixture was left to stand, and it deposited a white powder which was filtered off and dried, to give 1,3-bis[2-(2-quanidinothiazol-4-ylmethylthio)ethyl]thiourea dihydrochloride monohydrate, m.p. 144°–147° C.

EXAMPLE 2

A mixture of 2-quanidino-4-(4-aminobutyl)thiazole (0.105 g) and 1-[4-(2-guanidinothiazol-4-yl)butylamino]-2-methoxycyclobutene-3,4-dione (0.16 g) in dry methanol (5 ml) was stirred for 18 hours at room temperature. The white solid was filtered off, washed with methanol and dried in vacuo to give 1,2-bis[4-(2-guanidinothiazol-4-yl)-butylamino]cyclobutene-3,4-dione, 0.16 g., m.p. 228°–229° C.

EXAMPLE 3

A mixture of 2-guanidino-4-[(2-aminoethyl)-thiomethyl]thiazole dihydrochloride (0.024 g), 1-[4-(2-guanidinothiazol-4-yl)butylamino]-2-methoxycyclobutene-3,4-dione (0.032 g) and triethylamine (0.03 ml) in dry methanol (1 ml) was stirred for 18 hours at room temperature. The white solid was filtered off, washed with methanol and dried in vacuo to give 1-[2-(2-guanidinothiazol-4-ylmethylthio)ethylamino]-2-[4-(2-guanidinothiazol-4-yl)butylamino]cyclobuten-3,4-dione, (0.022 g), m.p. 208°–210°.

EXAMPLE 4

A mixture of 2-guanidino-4-[(2-aminoethyl)thiomethyl]thiazole dihydrochloride (0.66 g), triethylamine (1.04 g), carbonyl di-imidazole (0.49 g) and dimethyl formamide (25 ml) was stirred at room temperature overnight. After filtration, the solution was evaporated to dryness under reduced pressure. The residue was suspended in water (25 ml) containing aqueous ammonia (s.g. 0.88; 5 ml), the mixture extracted with ethyl acetate (2×20 ml) and the combined extracts washed with water (50 ml), dried (MgSO$_4$), filtered and evaporated to dryness. The residual gum was dissolved in acetone (10 ml) containing isopropanol (2 ml) and added to a solution of maleic acid (0.28 g) in acetone (10 ml). The white precipitate was filtered off, washed with acetone and dried to give 1,3-bis[2-(2-guanidinothiazol-4-ylmethylthio)ethyl]urea dimaleate, m.p. 109°–113°.

EXAMPLE 5

A mixture of 2-(2-guanidinothiazol-4-ylmethylthio)ethyl isothiocyanate hydrogen maleate (0.712 g), 4-(2-aminoethyl)imidazole dihydrochloride (histamine dihydrochloride) (0.404 g), triethylamine (0.808 g) and methanol (35 ml) was stirred at room temperature overnight. The mixture was purified by preparative thin layer chromatography on Merck 60 F-254 plates using as solvent ethyl acetate/ethanol/ammonia (s.g. 0.88) 6:1:1 v/v/v, eluting the band of $R_F$ 0.4 from the plates with ethanol. Evaporation of the filtered extract followed by treatment with maleic acid in acetone gave a white solid which was filtered off and washed with acetone followed by a little cold ethanol to give 1-[2-(2-guanidinothiazol-4-ylmethylthio)ethyl]-3-[2-(imidazol-4-yl)ethyl]thiourea dimaleate hemihydrate, m.p. 100° C. (decomp.).

The 2-(2-guanidinothiazol-4-ylmethylthio)ethyl isothiocyanate used as starting material may be prepared as follows:

A solution of thiophosgene (1.55 g) in methylene chloride (60 ml) was added dropwise to a vigorously stirred ice-cooled mixture of 2-guanidino-4-[(2-aminoethyl)-thiomethyl]thiazole dihydrochloride (6.08 g), triethylamine (8.5 g), water (20 ml) and methylene chloride (45 ml). Stirring was continued for 2 hours. The mixture was filtered through diatomaceous earth, the layers separated and the aqueous layer extracted with more methylene chloride (2×50 ml). The combined extracts were washed with water (30 ml), dried ($MgSO_4$), filtered and evaporated to dryness. The residue was dissolved in acetone (25 ml) and added to a solution of maleic acid (2.0 g) in acetone (20 ml). After one hour, the precipitate was filtered off and washed with acetone to give 2-(2-guanidinothiazol-4-yl-methylthio)ethyl isothiocyanate hydrogen maleate as a pale yellow solid, m.p. 152°–3° C. After recrystallization from ethanol (charcoal) the m.p. was 158°–160° C.

EXAMPLE 6

A mixture of 2-(2-guanidinothiazol-4-ylmethylthio)ethyl isothiocyanate hydrogen maleate (0.778 g), triethylamine (1.0 g), 5-methyl-4-[(2-aminoethyl)thiomethyl]imidazole (0.364 g) and methanol (20 ml) was stirred at room temperature overnight. The mixture was poured into water (60 ml), extracted with ethyl acetate (2×50 ml), the combined extracts washed with water (25 ml), dried ($MgSO_4$), filtered and evaporated to dryness. The residue was dissolved in acetone (10 ml) and added to a solution of maleic acid (0.28 g) in acetone (10 ml). The precipitate was filtered off and recrystallized from ethanol (charcoal) to give 1-[2-(2-guanidinothiazol-4-ylmethylthio)ethyl]-3-[2-(5-methylimidazol-4-ylmethylthio)ethyl]thiourea maleate as a white solid, m.p. 90°–93° (decomp.).

EXAMPLE 7

By the method of Example 5, using 3-(imidazol-4-yl)propylamine dihydrochloride instead of histamine dihydrochloride, there was obtained 1-[2-(2-guanidino-thiazol-4-ylmethylthio)ethyl]-3-[3-(imidazol-4-yl)propyl]-thiourea dimaleate hemihydrate, decomposing at about 120° after softening at 78°–84°.

EXAMPLE 8

A mixture of 1-benzoyl-3-[2-(2-guanidinothiazol-4-ylmethylthio)ethyl]thiourea (0.394 g), histamine dihydrochloride (0.276 g), triethylamine (0.20 g), silver nitrate (0.204 g) and dimethyl formamide (20 ml) was stirred at room temperature overnight. After filtration the solution was evaporated to dryness and the residue purified by preparative thin layer chromatography (Merck 60F-254 plates developed with ethyl acetate/ethanol/ammonia (s.g. 0.88) 6:1:1 v/v/v). Isolation of the main band ($R_F$ 0.3) gave an oil which crystallized on trituration with acetone to give 1-benzoyl-2-[2-(2-guanidinothiazol-4-ylmethylthio)ethyl]-3-[2-(imidazol-4-yl)ethyl]guanidine, decomposing at 147°–150° after softening at 115°–117°.

The 1-benzoyl-3-[2-(2-guanidinothiazol-4-yl-methylthio)ethyl]thiourea used as starting material may be prepared as follows:

A solution of benzoyl isothiocyanate (6.48 g) in dimethyl formamide (15 ml) was added to a stirred mixture of 2-guanidino-4-[(2-aminoethyl)thiomethyl]-thiazole dihydrochloride (12.16 g) and triethylamine (8.08 g) in dimethyl formamide (240 ml). The mixture was left to stand for 3 days, and then poured into hot water (50°; 2 l.). The mixture was stirred for 15 minutes, filtered and the residue air-dried to give a white solid.

EXAMPLE 9

A solution of 2-guanidino-4-[(2-(2-cyano-2-methylisothioureido)ethylthiomethyl]thiazole (0.5 g) and 2-[5-dimethylaminomethylfuran-2-ylmethylthio]ethylamine (0.33 g) in acetonitrile (10 ml) was heated under reflux for 48 hours. A further portion of 2-[5-dimethylaminomethylfuran-2-ylmethylthio]ethylamine (0.5 g) was added and the mixture was heated under reflux for 16 hours. The mixture was evaporated to dryness and the residue was partitioned between water and ethyl acetate. The ethyl acetate layer was dried with anhydrous magnesium sulphate and evaporated. The residual gum was triturated four times with warm diethyl ether (10 ml). The residue was further purified by applying to Merck 60 F254 preparative plates and eluting with acetonitrile/ammonia (s.g. 0.880) 7:1 v/v. The product was redissolved in acetonitrile (5 ml), and the solution filtered and evaporated to give 2-quanidino-4-[2-(2-cyano-3-[2-(5-dimethylaminomethylfuran-2-ylmethylthio)ethyl]guanidino)-ethylthiomethyl]thiazole as pale brown gum (0.15 g).

The n.m.r. spectrum in $d_6$ dimethyl sulphoxide/$CDCl_3$ using tetramethylsilane as an internal standard ($\delta = 0$) had the following resonances ($\delta$): 2.25 (singlet, 6H); 2.7 (multiplet, 4H+DMSO); 2.9 (broad singlet, $H_2O$); 3.35 (multiplet, 6H); 3.6 (singlet, 2H); 3.8 (singlet, 2H); 6.2 (quartet, 2H); 6.4 (multiplet, 7H).

EXAMPLE 10

A mixture of 2-quanidino-4-[2-(3-cyano-2-methylisothioureido)ethylthiomethyl]thiazole (3.3 g) and 1,3-diamino-2-hydroxypropane (3.6 g) in ethanol (25 ml) was heated under reflux for 3.5 hours. The solution was evaporated to dryness and the residue purified by column chromatography on silica eluted with chloroform/methanol/aqueous ammonia (s.g. 0.88) 7:3:0.5 v/v/v to give the main fraction as a white foam. A sample of this product (0.3 g) was mixed with 2-(2-guanidinothiazol-4-ylmethylthio)ethyl isothiocyanate hydrogen maleate (0.32 g) and triethylamine (0.3 ml) in ethanol (10 ml). Enough methanol was then added to give a clear solution, and the mixture was allowed to stand at room temperature overnight. The mixture was evaporated to dryness and the residue purified by column chromatography on silica eluted with chloroform/methanol/aqueous ammonia (s.g. 0.88) 4:1:0.5 v/v/v to give the main product as a white foam, which was dissolved in ethanol (15 ml) and added to a solution of maleic acid (0.08 g) in ethanol (5 ml). The precipitate was filtered off and recrystallized from ethanol to give 1-[2-(2-guanidinothiazol-4-ylmethylthio)ethyl]-3-[3-(2-cyano-3-(2-(2-guanidino-thiazol-4-ylmethylthio)ethyl)-guanidino)-2-hydroxypropyl]thiourea dimaleate (containing half a mole of ethanol of crystallization), m.p. 145°–148°.

EXAMPLE 11

A mixture of 1-[2-(2-guanidinothiazol-4-ylmethylthio)ethylamino]-2-methoxycyclobutene-3,4-dione (0.17 g), 4-aminomethylpyridine (0.054 g), methanol (5 ml) and dimethyl formamide (3 ml) was stirred at room temperature for seven days. Evaporation of the solution gave a yellow oil which crystallized on scratching; this was triturated with ethanol and filtered to give 1-[2-(2-guanidinothiazol-4-ylmethylthio)ethylamino]-2-(4-pyridylmethylamino)-cyclobutene-3,4-dione; m.p. 172°–175°.

The 1-[2-(2-guanidinothiazol-4-ylmethylthio)-ethylamino]-2-methoxycyclobutene-3,4-dione used as starting material may be prepared as follows:

A mixture of 2-guanidino-4-[(2-aminoethyl)thiomethyl]thiazole dihydrochloride (0.606 g), 1,2-dimethoxycyclobutene-3,4-dione (0.284 g), triethylamine (0.56 ml) and methanol (10 ml) were stirred at room temperature for one hour. The precipitated solid was filtered off and washed with methanol to give white crystals, m.p. 183°–185°.

EXAMPLE 12

A pharmaceutical tablet composition containing a derivative of formula I may be prepared by combining, mixing and compressing the following ingredients into slugs:

| | |
|---|---|
| 1,3-bis[2-(2-guanidinothiazol-4-ylmethylthio)ethyl]-thiourea | 100 g |
| Starch | 102 g |
| Powdered Lactose | 102 g |
| Talc | 26 g |
| Total | 330 g |

The slugs should then be ground to form granules that will pass through a 14 to 16 mesh screen. The granules may then be recompressed into about 1000 tablets using a suitable compression mold to form tablets.

What is claimed is:

1. A guanidine derivative of the formula I:

$$\text{Het}^1\text{-(CH}_2)_m\text{-Y}^1\text{-(CH}_2)_n\text{-NR}^1\text{-A-NR}^2\text{-(CH}_2)_q\text{-Y}^2\text{-(CH}_2)_p\text{-Het}^2 \quad \text{I}$$

in which
$Y^1$ and $Y^2$, which may be the same or different, are oxygen or sulphur atoms, direct bonds or methylene or sulphinyl radicals;
m and p, which may be the same or different, are 0 to 4 and
n and q, which may be the same or different, are 1 to 4,
provided that when $Y^1$ or $Y^2$ is an oxygen or sulphur atom or a sulphinyl radical, m or p respectively is 1 to 4 and provided that when $Y^1$ or $Y^2$ is an oxygen atom or a sulphinyl radical, n or q respectively is 2 to 4;
one of $R^1$ and $R^2$ is a hydrogen atom and the other is a hydrogen atom or an alkyl radical of 1 to 6 carbon atoms;
A is a 3,4-dioxocyclobuten-1,2-diyl radical or a radical of the formula C=Z in which Z is a sulphur or oxygen atom or a radical of the formula NCN, $NNO_2$, $CHNO_2$, $NCONH_2$, $C(CN)_2$, $NCOR^3$, $NCO_2R^3$, $NSO_2R^3$ or $NR^4$ in which $R^3$ is an alkyl radical of 1 to 6 carbon atoms, an aryl radical of 6 to 12 carbon atoms or an alkylphenyl radical of 7 to 12 carbon atoms and $R^4$ is a hydrogen atom or an alkyl radical of 1 to 6 carbon atoms; or when $R^1$ and $R^2$ are both hydrogen atoms -A- represents a radical of the formula II:

$$\text{-A}^1\text{-E}^1\text{-G-E}^2\text{-A}^2\text{-} \quad \text{II}$$

in which $A^1$ and $A^2$, which may be the same or different, are 3,4-dioxocyclobuten-1,2-diyl radicals or radicals of the formula $C=Z^1$ and $C=Z^2$ respectively in which $Z^1$ and $Z^2$, which may be the same or different, have one of the values given above for Z; $E^1$ and $E^2$, which may be the same or different, are oxygen or sulphur atoms or NH radicals optionally substituted by alkyl radicals of 1 to 10 carbon atoms, alkenyl or alkynyl radicals of 3 to 10 carbon atoms in which the double or triple bond respectively is separated from the nitrogen atom to which the radical is attached by at least one carbon atom, cycloalkyl radicals of 3 to 8 carbon atoms, (primary hydroxy)alkyl radicals of 2 to 6 carbon atoms, alkoxyalkyl radicals of 3 to 10 carbon atoms in which the oxygen atom is separated from the nitrogen atom to which the radical is attached by at least two carbon atoms, or alkylamino or dialkylamino radicals of 3 to 10 and 4 to 10 carbon atoms respectively in which the nitrogen atom is separated from the nitrogen atom to which the radical is attached by at least two carbon atoms; and G is an alkylene radical of 2 to 12 carbon atoms, an alkenylene or alkylene radical of 4 to 12 carbon atoms in which the double and triple bonds respectively are separated from $E^1$ and $E^2$ by at least one carbon atom, or a hydroxyalkylene radical of 3 to 12 carbon atoms in which the hydroxy substituent is carried on a carbon atom which is separated from $E^1$ and $E^2$ by at least one carbon atom;

$Het^1$ is an oxazol-4-yl, thiazol-4-yl or imidazol-4-yl radical substituted in the 2-position by a radical of the formula III:

or $Het^1$ is a 1,2,4-thiadiazol-3-yl or 1,2,4-oxadiazol-3-yl radical substituted in the 5-position by a radical of the formula III, in which $R^5$ is a hydrogen atom, an alkyl radical of 1 to 10 carbon atoms, an alkanoyl radical of 1 to 6 carbon atoms or an aroyl radical of 7 to 11 carbon atoms;

$Het^2$ is independently one of the values given above for $Het^1$;

provided that when $R^1$ and $R^2$ are both hydrogen atoms and A is C=NH, $Y^1$ and/or $Y^2$ is a sulphur atom;

and the pharmaceutically-acceptable acid-addition salts thereof.

2. The guanidine derivative as claimed in claim 1, in which
one of $R^1$ and $R^2$ is a hydrogen atom and the other is a hydrogen atom or a methyl radical;
A is a 3,4-dioxocyclobuten-1,2-diyl radical or a radical of the formula C=Z in which Z is a sulphur or oxygen atom or a radical of the formula NCN, $NNO_2$, $CHNO_2$, $NCONH_2$, $C(CN)_2$, $NCOR^3$, $NCO_2R^3$, $NSO_2R^3$ or $NR^4$ in which $R^3$ is a methyl, phenyl or p-tolyl radical and $R^4$ is a hydrogen atom or a methyl radical, or when $R^1$ and $R^2$ are both hydrogen atoms, -A- represents a radical of the formula II:

$$\text{-A}^1\text{-E}^1\text{-G-E}^2\text{-A}^2\text{-} \quad \text{II}$$

in which $A^1$ and $A^2$ are as defined in claim 1;

$E^1$ and $E^2$, which may be the same or different are oxygen or sulphur atoms or NH radicals optionally substituted by methyl, ethyl, n-propyl, i-propyl, n-hexyl, allyl, propargyl, cyclopropyl, cyclohexyl, 2-hydroxyethyl, 3-hydroxypropyl, 2-methoxyethyl, 2-methylaminoethyl or 2-dimethylaminoethyl radicals; and G is an ethylene, trimethylene, tetramethylene, but-2-enylene, but-2-ynylene or 2-hydroxytrimethylene radical;

$R^5$ in formula III is a hydrogen atom or a methyl, n-butyl, acetyl or benzoyl radical;

$Het^2$ is an oxazol-4-yl, thiazol-4-yl or imidazol-4-yl radical substituted in the 2-position by a radical of the formula III given in claim 1 or a 1,2,4-thiadiazol-3-yl or 1,2,4-oxadiazol-3-yl radical substituted in the 5-position by a radical of the formula III given in claim 1.

3. The guanidine derivative as claimed in claim 1, in which A is a 3,4-dioxocyclobuten-1,2-diyl radical or a radical of the formula C=Z in which Z is a radical of the formula NCN, $NNO_2$, $CHNO_2$ or $NCONH_2$.

4. The guanidine derivative as claimed in claim 1, in which $Het^1$ and $Het^2$, $Y^1$ and $Y^2$, $R^1$ and $R^2$, m and p and n and q are the same.

5. The guanidine derivative as claimed in claim 1, in which $Het^1$ is a 2-guanidinothiazol-4-yl or a 5-guanidino-1,2,4-thiadiazol-3-yl radical.

6. The guanidine derivative as claimed in claim 1, in which $Y^1$ is a sulphur atom or methylene radical, m is 1 and n is 2 and $Y^2$ is a sulphur atom or a methylene radical, p is 1 and q is 2.

7. The guanidine derivative as claimed in claim 1, in which $Het^2$ is a 2-guanidinothiazol-4-yl or 5-guanidino-1,2,4-thiadiazol-3-yl radical.

8. A guanidine derivative selected from 1,3-bis[2-(2-guanidinothiazol-4-ylmethylthio)ethyl]thiourea;

1,2-bis[4-(2-guanidinothiazol-4-yl)butylamino]cyclobutene-3,4-dione;

1-[2-(2-guanidinothiazol-4-ylmethylthio)ethylamino]-2-[4-(2-guanidinothiazol-4-yl)butyl-amino]cyclobutene-3,4-dione;

1-[2-(2-guanidinothiazol-4-ylmethylthio)ethyl]-3-[3-(2-cyano-3-(2-(2-guanidinothiazol-4-ylmethylthio)ethyl)guanidino)-2-hydroxypropyl]thiourea, and the pharmaceutically-acceptable acid-addition salts thereof.

9. A pharmaceutical composition to inhibit gastric acid secretion which comprises a guanidine derivative as claimed in claim 1 in association with a pharmaceutically-acceptable diluent or carrier.

10. A method of inhibiting gastric acid secretion in a living animal which comprises administering to the animal a therapeutically effective amount of the composition of claim 9.

11. The guanidine derivative as claimed in claim 1, in which $Het^1$ and $Het^2$ are 2-guanidinothiazol-4-yl radicals.

* * * * *

UNITED STATES PATENT AND TRADEMARK OFFICE
CERTIFICATE OF CORRECTION

PATENT NO. : 4,309,435
DATED : January 5, 1982
INVENTOR(S) : Tobias O. Yellin and David J. Gilman It is certified that error appears in the above-identified patent and that said Letters Patent are hereby corrected as shown below:

Column 14, line 22, "or alkylene" should read --or alkynylene--.

Signed and Sealed this

Seventeenth Day of April 1984

[SEAL]

Attest:

GERALD J. MOSSINGHOFF

Attesting Officer     Commissioner of Patents and Trademarks